United States Patent [19]

Grace, Jr. et al.

[11] 4,252,965

[45] Feb. 24, 1981

[54] PROCESS FOR THE PRODUCTION OF 1-SUBSTITUTED-3-HYDROXY-5-CHLORO-1,2,4-TRIAZOLES

[75] Inventors: Henry C. Grace, Jr.; Melvin J. Guillory, Jr., both of Baton Rouge, La.

[73] Assignee: Ciba-Geigy Corporation, Ardsley, N.Y.

[21] Appl. No.: 55,115

[22] Filed: Jul. 5, 1979

[51] Int. Cl.³ .......................................... C07D 249/12
[52] U.S. Cl. .................................................... 548/263
[58] Field of Search ......................................... 548/263

[56] References Cited

U.S. PATENT DOCUMENTS 3,867,396  2/1975  Dawes et al. ........................ 548/263
3,992,398  11/1976  Böhner et al. ....................... 548/263

Primary Examiner—Alton D. Rollins
Attorney, Agent, or Firm—Karl F. Jorda

[57] ABSTRACT

An improved process is provided for the production of 1-substituted-3-hydroxy-5-chloro-1,2,4-triazoles which involves reacting in dilute solution a 1-substituted-1-cyanohydrazine with phosgene in tetrahydrofuran as the specific inert solvent, treating the reaction mixture with anhydrous ammonia to form an ammonium salt of the 1,2,4-triazole, said ammonium salt being insoluble in tetrahydrofuran, and liberating from said isolated salt the 1,2,4-triazole in yields from about 85 to 92% of theory and in very pure state by treating said salt with an acid. The 1,2,4-triazoles are valuable intermediates in the manufacture of pesticides.

3 Claims, No Drawings

PROCESS FOR THE PRODUCTION OF 1-SUBSTITUTED-3-HYDROXY-5-CHLORO-1,2,4-TRIAZOLES

DETAILED DISCLOSURE

The present invention relates to an improved process for the production of a 1-substituted-3-hydroxy-5-chloro-1,2,4-triazole compound of the formula

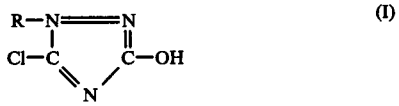  (I)

wherein R represents lower alkyl, cycloalkyl or aryl. These compounds are valuable intermediates in the manufacture of pesticides. They can be converted by reaction with phosphoric acid ester halides or thiophosphoric acid ester halides into phosphoric or thiophosphoric acid esters, respectively, which have excellent insecticidal action. Such compounds are disclosed in U.S. Pat. Nos. 3,867,396 and 3,932,629.

In the above definition of R, lower alkyl has from 1–5 carbon atoms and is, for instance, methyl, ethyl, propyl, isopropyl, n-butyl, iso-butyl, sec.-butyl, n-pentyl, isopentyl or neo-pentyl; cycloalkyl has from 3–7 carbon atoms and is, for instance, cyclopropyl, cyclopentyl, cyclohexyl or cycloheptyl; aryl is for instance, unsubstituted naphthyl, such as, 1-naphthyl or 2- naphthyl or unsubstituted phenyl, or naphthyl or phenyl substituted by lower alkyl, lower alkoxy, halogen, nitro or cyano groups; lower alkyl having the meaning given above, lower alkoxy having from 1–4 carbon atoms and being, for instance, methoxy, ethoxy, n-propoxy, i-propoxy, n-butoxy, sec-butoxy or i-butoxy; halogen denoting chlorine, fluorine or bromine and particularly chlorine.

According to the improved process of the present invention a compound of the formula (II)

  (II)

wherein R has the meaning given under formula (I), is reacted with phosgene using tetrahydrofuran as specific solvent. According to a preferred mode of the improved process a 4–10 percent solution of a compound of the formula (II) in tetrahydrofuran is reacted with phosgene. More specifically, a 6–8 percent solution (weight by volume) of a compound of the formula (II) in tetrahydrofuran is employed. The reaction temperature is between −10° and 50° C., preferably between −5° and 40° C. and still more preferably between 0° and 30° C. The reaction mixture obtained is treated with ammonia to form an ammonium salt of a compound of the formula (I), as defined above.

The ammonia is preferably employed in gaseous and anhydrous form but can also be in anhydrous liquid form. By introducing anhydrous ammonia into the tetrahydrofuran solution containing the reaction mixture, the novel ammonium salt of a compound of the formula (I) precipitates. This can be isolated in pure state by filtering, washing the precipitate with tetrahydrofuran or other suitable solvent and drying the product. From such a salt of a compound of the formula (I) the compound itself is liberated in high yield and very pure state by treating an aqueous solution of the salt with an acid, such as a mineral acid, e.g., hydrochloric acid, sulfuric acid, or phosphoric acid, in excess. Preferably, hydrochloride acid is used.

According to the improved process of the present invention a compound of the formula (I) may be obtained in yields ranging from about 85–92% of theory and in very pure state, such as for instance, of 98% assay.

According to the closest prior art process disclosed in U.S. Pat. No. 3,992,398, 1-alky-3-hydroxy-5-chloro-1,2,4-triazoles of the formula

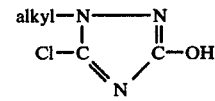

wherein alkyl represents a straight-chain or branched-chain alkyl group having 1–5 carbon atoms, are produced by reacting a compound of the formula

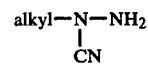

wherein alkyl has the meaning given above, with phosgene in an inert solvent, e.g., aliphatic, aromatic or halogenated hydrocarbon, ethers or ethereal compounds, dialkylated amides, sulphoxides, nitriles, and ketones, with methylene chloride or dioxane being preferred, at a temperature of between 0° and 180° C., preferably between 20° and 130° C., and a 1-alkyl-3-hydroxy-5-chloro- 1,2,4-triazole of the formula as defined above is isolated, preferably in the form of a hydrochloride, with the yields varying in the range of between 53.2% and 79.5% of theory.

The ammonium salts of the compounds of formula I are not only novel but are particularly useful and advantageous in the present process in conjunction with the use of tetrahydrofuran as specific solvent. Of particular importance is the fact that isolation of compounds of formula I as their ammonium salts allows recycle of the dry tetrahydrofuran solvent to the reactor with minimum cleanup. Use of other bases to accomplish this either leaves large quantities of the product salt in the tetrahydrofuran solution or contaminates the tetrahydrofuran with water. Wet tetrahydrofuran cannot be recycled to the reactor; it must first go through a complicated double distillation under pressure which requires special equipment and significantly increases costs. The use of tetrahydrofuran under the very specific, relatively low temperature and high dilution conditions to achieve superior yields, especially in conjunction with the ammonium salt isolation technique, is also a significant feature of the subject process.

A preferred embodiment of the improved process according to the present invention comprises reacting 1-isopropyl-1-cyanohydrazine in the form of a 6–8 percent solution in tetrahydrofuran with phosgene at a temperature of between 0°–30° C., treating the reaction mixture with anhydrous ammonia to form the ammonium salt of 1-isopropyl-3-hydroxy-5-chloro-1,2,4-triazole, which precipitates almost totally from the tetrahydrofuran reaction mass, and liberating from said isolated salt 1-isopropyl-3-hydroxy-5-chloro-1,2,4-triazole in a yield ranging from 85.8–92.1% of theory and in a very pure state, such as of 98% assay, by treating it with 32–37% hydrochloric acid.

The following examples will serve to illustrate the improved process. The temperatures are given in degrees centigrade.

EXAMPLE 1

A 300-gallon, glass-lined, jacketed and agitated reactor is charged with 800 pounds of dry tetrahydrofuran (THF) and cooled below 0°. Liquid phosgene weighing 230 pounds is then transferred to the reactor with appropriate safety precautions and dissolved in the THF. To a 50-gallon, stainless steel, agitated hold tank is charged 74 pounds of dry THF (874 pounds total) and 178 pounds of 1-isopropyl-1-cyanohydrazine (IPCH), calculated as 100% material (this is an equivalent 16.9% IPCH in the total THF). The main reactor is further cooled to −15° and then the IPCH solution is slowly charged. The temperature is allowed to rise to 12°–14° where it is maintained by regulating the IPCH solution feed rate. After the IPCH feed is complete, the temperature is allowed to rise to 20°–25° and is maintained by regulating the IPCH solution feed rate. After the IPCH feed is complete, the temperature is allowed to rise to 20°–25° and is maintained for four hours. Next, 110 pounds of anhydrous ammonia is slowly sparged in with good agitation to destroy the phosgene and precipitate the ammonium salt of 1-isopropyl-3-hydroxy-5-chloro-1,2,4-triazole (IHCT.NH$_3$). The entire reaction mass is then pressure-filtered, and the wet cake is washed with 100 pounds of fresh THF and dried under vacuum to recover THF. The dry solid is dissolved in 115 gallons of water, to which is then added 93 gallons of ethylene dichloride (EDC). Next about 143 pounds of 32% HCl is slowly charged to drop the pH to 1 to 2. The EDC layer containing the product is removed and analyzed for use in the next step. Yield: about 75% of IHCT assaying 98–99.5% on a solvent-free basis.

EXAMPLE 2

A jacketed resin kettle is charged with 800 g of dry tetrahydrofuran (THF) and cooled to 0° with circulating brine. Then 76.6 g of phosgene is sparged into the THF and dissolved. A mixture of 67.57 g of 87.2% 1-isopropyl-1-cyanohydrazine (IPCH) in 53 g of dry THF is slowly dropped into the reactor over 17 minutes. A maximum temperature of 3° is allowed. After IPCH addition, the reactor is held one hour at 0° and then three hours at 20°. Anhydrous ammonia weighing about 36.4 g is then sparged slowly into the reactor holding 25° maximum. The resulting slurry is filtered in a Gelman pressure filter and dried in vacuo on the filter with gentle heating. The cake is dissolved in about 200 ml of water, to which 400 ml of ethylene dichloride (EDC) is then added. Next, 37% HCl is added to release 1-isopropyl-3-hydroxy-5-chloro-1,2,4-triazole (IHCT) into the EDC layer at pH 1–2. The EDC is stripped off under vacuum, leaving IHCT 86.7% yield with an assay of 99.2%. (This was an equivalent 6.4% IPCH in THF).

EXAMPLE 3

A jacketed reactor is charged with 3,137 ml of tetrahydrofuran and the mass is chilled to −5°. Gaseous phosgene (263.5 g) is sparged into the stirred solvent. Following this, a solution of 232.7 g of 87.2% 1-isopropyl-1-cyanohydrazine in 209 ml tetrahydrofuran (THF) is added over 35 minutes. After three hours at 20° the reaction mixture is quenched by the addition of anhydrous ammonia in excess, whereafter 1-isopropyl-3-hydroxy-5-chloro-1,2,4-triazole ammonium salt precipitates. The resulting slurry of said ammonium salt in THF is filtered and washed with fresh tetrahydrofuran. The wet filter cake is dissolved in 2 liters of water followed by stripping out the THF in form of its azeotrope with 1 mol water. The remaining solution is rendered acid to pH 1.0 with 37% hydrochloric acid, whereafter 1-isopropyl-3-hydroxy-5-chloro-1,2,4-triazole is obtained which is isolated by extraction with ethylene dichloride and evaporation of the resulting solution yielding 306.6 g (92.1% of theory) of the product of 99.4% purity). (This was an equivalent 6.8% IPCH in THF).

EXAMPLE 4

A jacketed resin kettle is charged with 974 ml of tetrahydrofuran (THF) and cooled to −5°. Gaseous phosgene (81.8 g) is sparged in over 30 minutes. Immediately after this a solution of 72.5 g of 87.2% 1-isopropyl-1-cyano-hydrazine in 65 ml of THF is charged to the reactor in 65 seconds. (This is 6.8% IPCH in the total THF present). THe temperature is controlled at 10° maxiumum. The reactor iis maintained at 10° for one hour followed by quenching with gaseous anhydrous ammonia, whereafter 1-isopropyl-3-hydroxy-5-chloro-1,2,4-triazole ammonium salt precipitates. The slurry is filtered and the filter cake is washed with three portions of ethylene dichloride (EDC—each 150 ml) to displace tetrahydrofuran in the filter. The filter cake is dissolved in 500 ml of water, and the pH of the solution is lowered to 1.0 by adding 37% hydrochloric acid. The mixture is treated with ethylene dichloride. Two more extractions using 50 ml of EDC are employed. The combined organic layers are stripped, leaving 1-isopropyl-3-hydroxy-5-chloro-1,2,4triazole of 98% assay, the yield being 92.5 g (88.2% of theory). The drry THF filtrate and EDC washings can be fractionally distilled to recover the anhydrous solvents.

EXAMPLE 5

A jacketed resin kettle is charged with 717 g of dry tetrahydrofuran (THF) and 14 g of ethylene dichloride (EDC) and cooled to 0°. Then 68.6 g phosgene is sparged in and dissolved in the solvent. A solution of 60.5 g of 87.2% 1-isopropyl-1-cyano-hydrazine (IPCH) in 48 g of dry THF is then charged to the reactor over 25 minutes while holding 0°. After charging IPCH, the reactor is held 35 minutes at 0° and three hours at 20°. Then 32.6 g of anhydrous ammonia is sparged into the reactor. The resulting slurry contains the ammonium salt of 1-isopropyl-3-hydroxy-5-chloro-1,2,4-triazole (IHCT.NH$_3$). Workup as in Example 2 produces an 87.9% yield of 99% assay IHCT.

What is claimed is:

1. In a process for the production of a 1-substituted-3-hydroxy-5-chloro-1,2,4-triazole compound of the formula

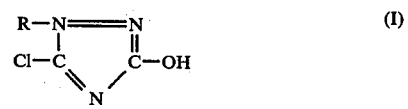

(I)

wherein R represents lower alkyl, cycloalkyl or aryl, which comprises reacting a compound of the formula

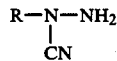 (II)

wherein R has the meaning given under formula (I), with phosgene in an inert solvent, treating the reaction mixture with an acid binding agent, rendering the reaction mixture acidic and isolating a compound of the formula (I), the improvement which consists in treating the reaction mixture with anhydrous ammonia to form an insoluble ammonium salt of a compound of the formula (I), isolating said salt and liberating from said salt a compound of the formula (I) with a mineral acid.

2. A process as claimed in claim 1 wherein R represents lower alkyl.

3. A process as claimed in claim 1 which comprises reacting 1-isopropyl-1-cyanohydrazine with phosgene treating the reaction mixture with anhydrous ammonia to form the ammonium salt of 1-isopropyl-3-hydroxy-5-chloro-1,2,4-triazole, isolating said salt, and liberating from said salt pure 1-isopropyl-3-hydroxy-5-chloro-1,2,4-triazole with hydrochloric acid.

* * * * *